(12) United States Patent
Keeble

(10) Patent No.: US 11,583,423 B2
(45) Date of Patent: Feb. 21, 2023

(54) EXPANDABLE TUBE FOR DEPLOYMENT WITHIN A BLOOD VESSEL

(71) Applicant: Oxford Endovascular Ltd., Oxford (GB)

(72) Inventor: Duncan Keeble, Newbury (GB)

(73) Assignee: Oxford Endovascular Ltd., Oxford (GB)

(*) Notice: Subject to any disclaimer, the term of this patent is extended or adjusted under 35 U.S.C. 154(b) by 102 days.

(21) Appl. No.: 16/576,444

(22) Filed: Sep. 19, 2019

(65) Prior Publication Data

US 2020/0008962 A1  Jan. 9, 2020

Related U.S. Application Data

(63) Continuation of application No. PCT/GB2018/050771, filed on Mar. 23, 2018.

(30) Foreign Application Priority Data

Mar. 24, 2017 (GB) ..................... 1704720

(51) Int. Cl.
*A61F 2/915* (2013.01)
*A61F 2/82* (2013.01)

(52) U.S. Cl.
CPC ........ *A61F 2/915* (2013.01); *A61F 2002/823* (2013.01); *A61F 2002/91575* (2013.01); *A61F 2230/0054* (2013.01)

(58) Field of Classification Search
CPC ............ A61F 2/915; A61F 2002/91575; A61F 2230/0054; A61F 2002/823; A61F 2/82; A61F 2/89
See application file for complete search history.

(56) References Cited

U.S. PATENT DOCUMENTS

2009/0024205 A1* 1/2009 Hebert .................. A61F 2/91
623/1.34
2009/0248136 A1 10/2009 Mews et al.
(Continued)

FOREIGN PATENT DOCUMENTS

CN 101083956 12/2007
CN 105167881 12/2015
(Continued)

*Primary Examiner* — Brian A Dukert
(74) *Attorney, Agent, or Firm* — Levine Bagade Han LLP

(57) ABSTRACT

An expandable tube for deployment within a blood vessel is disclosed. In one arrangement, the tube comprises an elongate frame that is reversibly switchable from a radially expanded and longitudinally contracted state to a radially contracted and longitudinally expanded state. The frame comprises a plurality of longitudinally deformable elements for providing longitudinal expansion and contraction of the frame and a plurality of circumferentially deformable elements for providing radial expansion and contraction of the frame. The longitudinally deformable elements can be expanded or contracted longitudinally substantially without any change in the shape of the circumferentially deformable elements. The plurality of circumferentially deformable elements comprises a plurality of sets of circumferentially deformable elements. Each set of circumferentially deformable elements forms a closed ring around an axis of elongation of the frame. Each closed ring consisting exclusively of the circumferentially deformable elements. At least two of the closed rings occupy overlapping ranges of longitudinal positions when the frame is in the radially expanded and longitudinally contracted state and occupy non-overlapping ranges of longitudinal positions when the frame is in the radially contracted and longitudinally expanded state.

18 Claims, 4 Drawing Sheets

(56) References Cited

U.S. PATENT DOCUMENTS

| | | |
|---|---|---|
| 2014/0277391 A1 | 9/2014 | Layman et al. |
| 2015/0190256 A1* | 7/2015 | Zhou .................. A61F 2/90 623/1.15 |
| 2016/0158036 A1* | 6/2016 | Loganathan .......... B23K 26/38 264/400 |
| 2016/0220396 A1 | 8/2016 | Zhou et al. |
| 2017/0035589 A1* | 2/2017 | Carpenter ............ A61F 2/013 |

FOREIGN PATENT DOCUMENTS

| | | |
|---|---|---|
| CN | 105517507 | 4/2016 |
| EP | 1707162 | 10/2006 |
| EP | 2098195 | 9/2009 |
| GB | 2494632 | 3/2013 |
| JP | 2011015704 | 1/2011 |
| WO | WO 2015/070124 | 5/2015 |

* cited by examiner

EXPANDABLE TUBE FOR DEPLOYMENT WITHIN A BLOOD VESSEL

CROSS-REFERENCE TO RELATED APPLICATIONS

This application is a continuation of International Patent Application Number PCT/GB2018/050771 filed Mar. 23, 2018, which claims priority to GB Patent Application Number 1704720.0 filed Mar. 24, 2017, the contents of which are incorporated herein by reference in their entirety.

BACKGROUND OF THE INVENTION

The present invention relates to an expandable tube for deployment within a blood vessel, particularly for use in redirecting blood flow away from an aneurismal sac.

An intracranial aneurysm is a weak region in the wall of an artery in the brain, where dilation or ballooning of the arterial wall may occur. Histologically, decreases in the tunica media, the middle muscular layer of the artery, and the internal elastic lamina cause structural defects. These defects, combined with hemodynamic factors, lead to aneurismal out-pouchings. Intracranial aneurysms are quite common diseases with a prevalence ranging from one to five percent among adult population according to autopsy studies. In the US alone, ten to twelve million people may have intracranial aneurysms.

Current methods for treating intracranial aneurysms include surgical clipping and endovascular coiling. In the surgical clipping method, the skull of the patient is opened, and a surgical clip is placed across the neck of the aneurysm to stop blood from flowing into the aneurysm sac. The risk of this method is relatively high, especially for elderly or medically complicated patients. Endovascular coiling is a less invasive method involving placement of one or more coils, delivered through a catheter, into the aneurysm until the sac of the aneurysm is completely packed with coils. It helps to trigger a thrombus inside the aneurysm. Although endovascular coiling is deemed to be safer than surgical clipping, it has its own limitations. First, after the aneurysm is filled with the coils, it will remain its original size. As a result, the pressure on the surrounding tissue exerted by the aneurysm will not be removed. Second, this procedure is not very effective for wide-necked aneurysms, where the coil is likely to protrude into the parent vessels. This problem may be mitigated by using a stent in combination with coiling embolization, but the procedure is difficult and time-consuming.

BRIEF SUMMARY OF THE INVENTION

Using an expandable tube, sometimes referred to as a stent, alone to treat the aneurysm is a promising way to avoid the problems stated above. In this method, a tube with an area of relatively low porosity is placed across the aneurysm neck in such a way as to redirect blood flow away from the sac and trigger formation of a thrombus within the aneurysm. Because the aneurysm solidifies naturally on itself, there is less danger of its rupture. Furthermore, because no coil is involved in this method, the aneurysm will gradually shrink as the thrombus is absorbed. Consequently, the pressure applied on the surrounding tissue can be removed. It is difficult, however, to manufacture a tube having optimal characteristics for this application. The tube has to be flexible enough to pass through and adapt to the shape of the very tortuous blood vessels in the brain while at the same time providing sufficient coverage (low porosity) to redirect blood flow away from the aneurysm to an adequate extent.

It is an object of the invention to provide an expandable tube for deployment within a blood vessel that has improved properties, particularly in the context of redirecting blood flow away from an aneurysm.

According to an aspect of the invention, there is provided an expandable tube for deployment within a blood vessel, comprising: an elongate frame that is reversibly switchable from a radially expanded and longitudinally contracted state to a radially contracted and longitudinally expanded state, wherein: the frame comprises a plurality of longitudinally deformable elements for providing longitudinal expansion and contraction of the frame and a plurality of circumferentially deformable elements for providing radial expansion and contraction of the frame; the longitudinally deformable elements can be expanded or contracted longitudinally substantially without any change in the shape of the circumferentially deformable elements; the plurality of circumferentially deformable elements comprises a plurality of sets of circumferentially deformable elements, each set of circumferentially deformable elements forming a closed ring around an axis of elongation of the frame, each closed ring consisting exclusively of the circumferentially deformable elements; and at least two of the closed rings occupy overlapping ranges of longitudinal positions when the frame is in the radially expanded and longitudinally contracted state and occupy non-overlapping ranges of longitudinal positions when the frame is in the radially contracted and longitudinally expanded state.

As compared to surgical clipping, the presently disclosed tube can be configured to redirect blood flow away from an aneurismal sac in a minimally invasive method that is much safer, has lower morbidity and mortality rates, requires less hospital stay and reduces the overall treatment cost. As compared to other minimally invasive methods, e.g. coiling embolization or stent-assisted coiling, the presently disclosed tube does not involve coils, which leads to several advantages, e.g. the mass effect of the aneurysm is reduced, and the tube is suitable for treating both saccular and fusiform aneurysms. As compared to current flow-diverters (i.e. stents configured to divert flow away from an aneurismal sac), the presently disclosed tube can provide higher radial strength, more controlled deployment and tailored surface coverage which is useful to prevent the blockage of branch blood vessels.

The provision of a frame that elongates as part of the radial contraction allows a high degree of radial contraction even when the frame is configured to present a low porosity in the radially expanded state. It is therefore possible to provide a frame that can be inserted into delivery catheters of very small diameter, for example less than 3 mm diameter, or more preferably less than 1 mm diameter. This property expands the range of clinical uses that are available.

The use of longitudinally overlapping closed rings of circumferentially deformable elements facilitates provision of low porosities in the radially expanded and longitudinally contracted state, which favours high radial strength and/or good flow redirection properties. This feature also allows the switching from the radially expanded and longitudinally contracted state to the radially contracted and longitudinally expanded state to be achieved without excessive strains in any portion of the frame.

In an embodiment, the closed rings form an alternating sequence of first type closed rings and second type closed rings, wherein: each of one or more of the circumferentially deformable elements on each first type closed ring is aligned in a direction parallel to the axis of elongation of the elongate frame with a corresponding identical one of the circumferentially deformable elements on each other first type closed ring and is not aligned with a corresponding identical one of the circumferentially deformable elements on any of the second type closed rings, when the frame is in the radially expanded and longitudinally contracted state.

This configuration reduces or avoids twisting of the tube during the switching from the radially expanded and longitudinally contracted state to the radially contracted and longitudinally expanded state. In an embodiment, twisting is further prevented by arranging for the longitudinally deformable elements to comprise sets of identical first type longitudinally deformable elements and sets of identical second type longitudinally deformable elements, wherein the sets of first type longitudinally deformable elements and the sets of second type longitudinally deformable elements are arranged in an alternating sequence such that each first type closed ring is connected to the next second type closed ring in a given direction parallel to the axis of elongation exclusively by first type longitudinally deformable elements and each second type closed ring is connected to the next first type closed ring in the same given direction parallel to the axis of elongation exclusively by second type longitudinally deformable elements, wherein the first type longitudinally deformable elements have a different shape and/or orientation from the second type longitudinally deformable elements, for example mirror images of each other when the frame is viewed in an unfolded planar state.

In an embodiment, each of one or more of the longitudinally deformable elements is curved along at least 20% of the length of the longitudinally deformable element. This helps to spread the strain over the longitudinally deformable element during the switching from the radially expanded and longitudinally contracted state to the radially contracted and longitudinally expanded state, allowing large overall deformations to be achieved without excessively stressing the longitudinally deformable elements.

In an embodiment, each of one or more of the longitudinally deformable elements is connected to one of the closed rings at a junction and configured such that an angle between the longitudinally deformable element and a circumferentially deformable element at the junction changes by less than 30 degrees during switching from the radially expanded and longitudinally contracted state to the radially contracted and longitudinally expanded state. This feature reduces undesirable stresses at the junction.

BRIEF DESCRIPTION OF THE SEVERAL VIEWS OF THE DRAWINGS

Embodiments of the invention will now be described, by way of example only, with reference to the accompanying drawings in which corresponding reference symbols indicate corresponding parts, and in which:

Embodiments of the invention provide a tube suitable for deployment within a blood vessel. The tube comprises an elongate frame 2. FIG. 1 depicts the outer geometry of the frame 2 in a radially expanded and longitudinally contracted state. FIG. 2 depicts the outer geometry of the frame 2 in a radially contracted and longitudinally expanded state. The frame 2 can be switched reversibly from the radially expanded and longitudinally contracted state shown in FIG. 1 to the radially contracted and longitudinally expanded state shown in FIG. 2.

Figure 1:
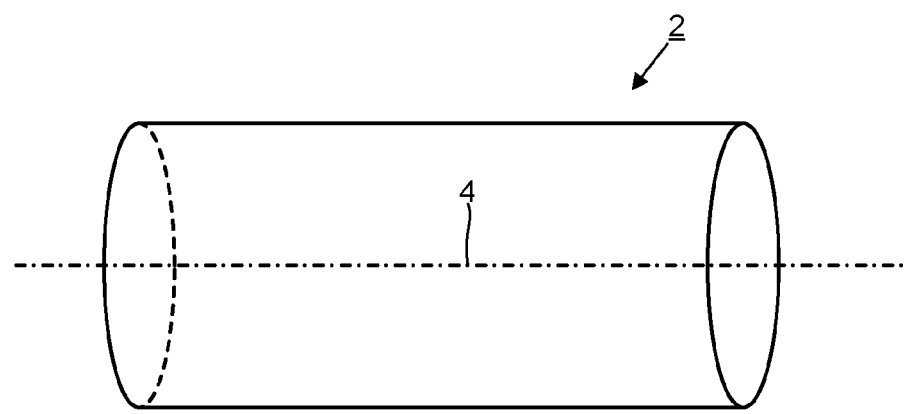
FIG. 1 is a schematic perspective view of the outer geometry of a tube in a radially expanded and longitudinally contracted state.
Figure 2:
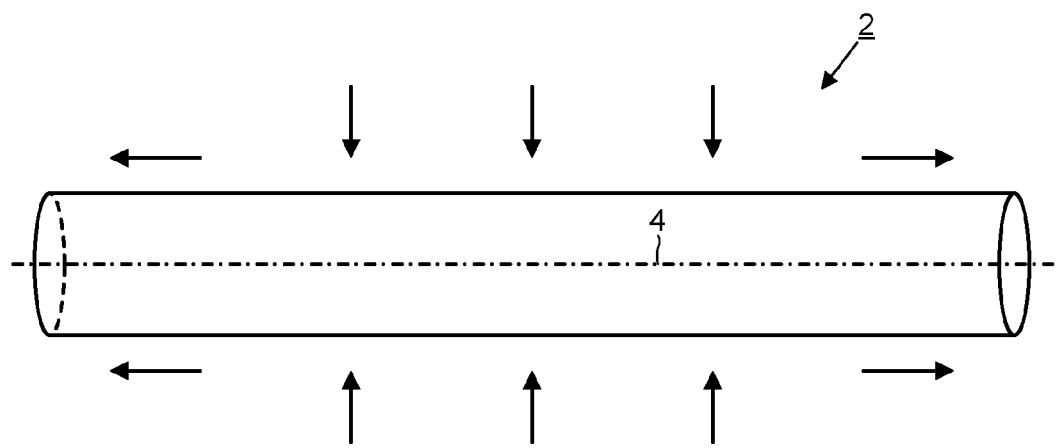
FIG. 2 is a schematic perspective view of the outer geometry of the tube of FIG. 1 in a radially contracted and longitudinally expanded state.

The frame 2 is expandable, optionally self-expanding. The frame 2 may comprise a shape memory alloy, for example, such as nitinol. Alternatively, the frame 2 may comprise a stainless steel, polymer or other biocompatible material.

The frame 2 is elongate relative to an axis of elongation 4. The frame 2 may be cylindrical for example. When the frame 2 is cylindrical, the maximum lateral dimension is the same at all positions and angles (i.e. it is equal to the diameter). When the frame 2 is not cylindrical the maximum lateral dimension may be different at different positions and/or angles. The maximum lateral dimension defines the minimum interior diameter of a cylindrical tube (e.g. a delivery catheter) that the frame could be inserted into.

In the radially contracted state the frame 2 is substantially narrower than in the radially expanded state. Preferably the maximum lateral dimension is 30% smaller in the radially contracted state, more preferably 50% smaller. Radially contracting the frame 2 allows the frame 2 to be inserted into a narrower delivery catheter for deployment at the site of interest. It is generally desirable for the delivery catheter to be as narrow as possible. This is particularly the case where access to a deployment site requires navigation of tortuous regions of vasculature. This may often be the case, for example, when treating a cerebral aneurysm.

DETAILED DESCRIPTION OF THE INVENTION

In the discussion below it is understood that the term porosity, p, refers to the ratio of the surface area of open regions to the total external surface area occupied by the frame or portion of frame that is being described. The total external surface area is the sum of the surface area of the open regions and the surface area of the regions occupied by the material of the frame. When the frame is cylindrical, the total external surface area is simply $2\pi \cdot R \cdot L$, where R is the radius of the cylinder and L is the length of the cylinder.

Consider a stent with a porosity $\rho$ in the fully radially expanded state. If the radius and length of the frame in the fully radially expanded state are $R_0$ and $L_0$, respectively, the minimum radius $R_{min}$ that the frame 2 can achieve in the radially contracted state, defined by the state in which the porosity becomes zero, is governed by $$R_{min} = \frac{(1-\rho)L_0}{L_1} \cdot R_0$$

where $L_1$ is the length of the frame in the radially contracted state. This relationship assumes that elements of the frame are not allowed to overlap with each other in the radial direction.

This relationship illustrates that if the length of the frame is not allowed to change to any significant extent, the radius can only reduce by a factor of $\rho$. As $\rho$ needs to be quite low (e.g. less than 80%, at least in a low porosity region, such as a region intended for positioning in use over the opening to an aneurismal sac), this represents a significant limitation to the extent to which the stent can be narrowed for insertion into a delivery catheter. For example, if the porosity $\rho$ of the frame is 20% and the length of the frame is not allowed to change during radial contraction, i.e. $L_1=L_0$, the frame can achieve only a maximum 20% reduction in radius. The provision of a frame that can expand longitudinally when adopting the radially contracted state is based on this understanding and allows much greater reductions in radius to be achieved. For example, if the length is allowed to double, i.e. $L_1=2 \cdot L_0$, the frame can achieve a 60% reduction in radius for a porosity of 20%.

Preferably, the frame 2 is configured so that it can be elongated by at least 25%, more preferably by at least 50%, even more preferably by 100% or 150%. Optionally, the elongation can be even longer, for example, 400%, 600%, 800%, or more.

Figure 3:
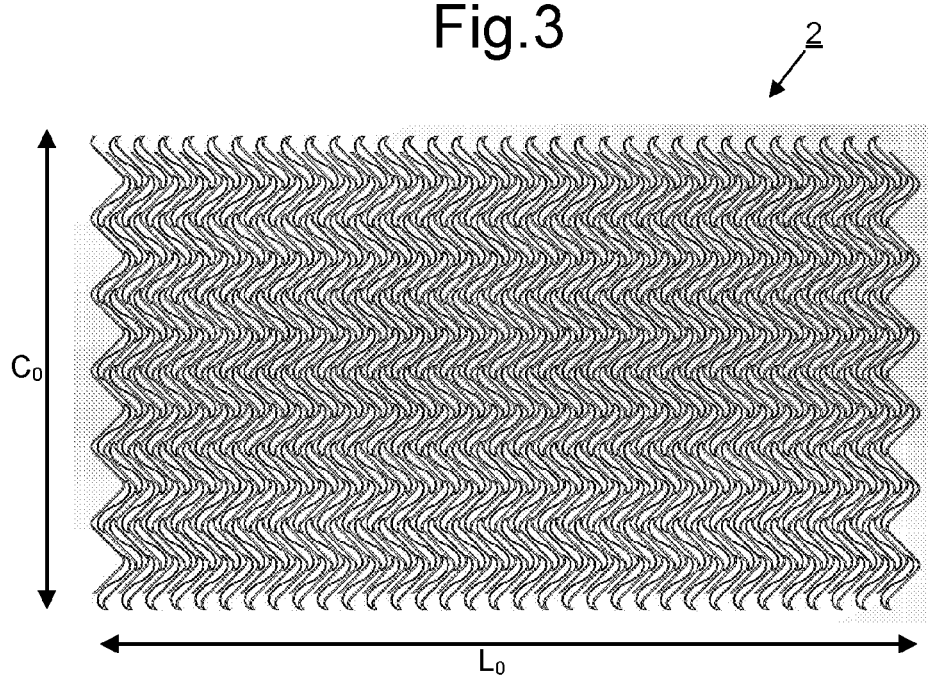
FIG. 3 is an unfolded view of an example frame in the radially expanded and longitudinally contracted state.

FIG. 3 shows an example frame 2 notionally unfolded so that it is flat (rather than cylindrical). The longitudinal axis runs horizontally in the plane of the page and the circumferential direction runs vertically in the plane of the page. The longitudinal length of the frame 2 is marked L0 and the circumferential length of the frame is marked C0.

Figure 4:
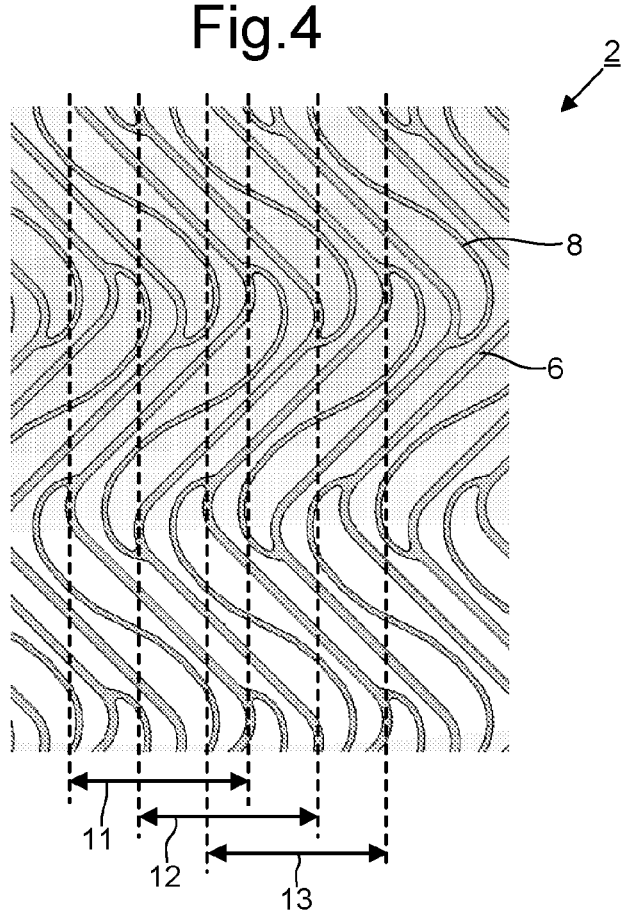
FIG. 4 depicts a portion of the frame of FIG. 3 illustrating closed rings of circumferentially deformable elements having overlapping ranges of longitudinal positions.

FIG. 4 is a magnified view of a portion of the frame 2 of FIG. 3. The frame 2 comprises a network of interconnecting arms. The interconnecting arms form a plurality of circumferentially deformable elements 6 for providing radial expansion and contraction of the frame 2. The frame 2 further comprises a plurality of longitudinally deformable elements 8, distinct from the circumferentially deformable elements 6, for providing longitudinal expansion and contraction of the frame 2. The circumferentially deformable elements 6 and the longitudinally deformable elements 8 may be connected together to form an integrally interconnected network, such that there are no material interfaces between any of the elements. The frame 2 may be formed for example by laser cutting a hollow tube, by 3D printing, or by other techniques known in the art for manufacturing such structures. All of the circumferentially deformable elements 6 and longitudinally deformable elements 8 may be provided at the same radius and, without any overlaps in the radial direction.

The plurality of circumferentially deformable elements 6 comprises a plurality of sets of circumferentially deformable elements 6. Each set of circumferentially deformable elements 6 forms a closed ring around the axis of elongation 4 of the frame 2. Each closed ring consists exclusively of the circumferentially deformable elements 6. In the example of FIGS. 3-8, each circumferentially deformable element 6 is substantially V-shaped. Each closed ring thus consists of a plurality of Vs connected together at the outer ends of the arms of each V.

Each of the closed rings occupies a range of longitudinal positions. In FIG. 4, three such ranges of positions are marked 11-13 for three different closed rings. It can be seen that the three ranges of longitudinal positions overlap with each other. This is a general characteristic of the frame 2 according to embodiments of the present disclosure: at least two of the closed rings should occupy overlapping ranges of longitudinal positions when the frame 2 is in the radially expanded and longitudinally contracted state. In the particular embodiment shown, each closed ring overlaps with four other closed rings. In general, each closed ring should overlap with at least one other closed ring, optionally at least two other closed rings.

Arranging for the closed rings to overlap in the radially expanded and longitudinally contracted state allows the frame to achieve a low porosity in this state. The low porosity may be suitable for example for redirecting blood flow away from an aneurismal sac and thereby promoting thrombus formation in the aneurismal sac. Preferably, the porosity is less than 90%, optionally less than 80%, optionally less than 70%, optionally less than 60%, optionally less than 50%.

Arranging for the closed rings to overlap in the radially expanded and longitudinally contracted state also helps to provide high radial stiffness by providing a high density of the circumferentially deformable elements per unit length. This may be useful when the tube is used to treat aneurysms and in other applications.

The frame 2 is further configured such that the closed rings that occupy overlapping longitudinal positions when the frame 2 is in the radially expanded and longitudinally contracted state occupy non-overlapping ranges of longitudinal positions when the frame 2 is in the radially contracted and longitudinally expanded state. Thus, the closed rings effectively move out of the way of each other and allow the frame to contract radially to a greater extent. This process is illustrated schematically in FIGS. 5 and 6.

Figure 5:
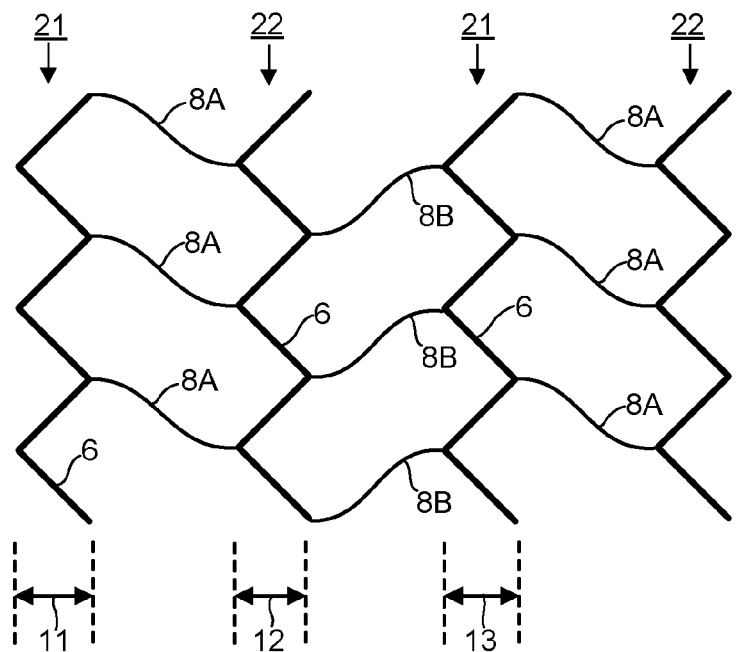
FIG. 5 schematically depicts expansion of longitudinally deformable elements substantially without any change in shape of circumferentially deformable elements in an unfolded view of a portion of a frame.

FIG. 5 depicts a portion of a frame 2 of the type depicted in FIG. 4 after longitudinal expansion of the frame 2. The longitudinal expansion can be achieved, at least partially, by longitudinal expansion of the longitudinal deformable elements 8A and 8B substantially without any change in the shape of the circumferential deformable elements 6 (forming closed rings 21 and 22). The longitudinal expansion results in the closed rings no longer overlapping with each other. The ranges of longitudinal positions 11-13 no longer overlap.

Figure 6:
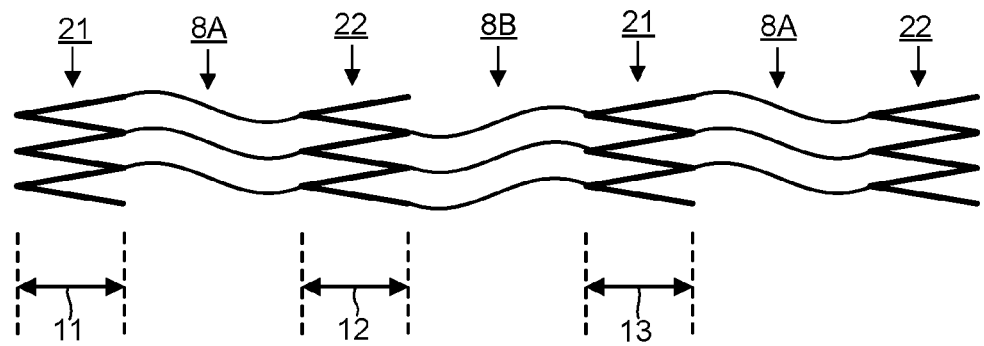
FIG. 6 schematically depicts radial contraction of the frame of FIG. 5.

FIG. 6 depicts the portion of the frame 2 of FIG. 5 after a subsequent radial contraction. The radial contraction is achieved principally or substantially entirely by deformation of the circumferentially deformable elements. In an embodiment, the deformation of the circumferentially deformable elements 6 occurs substantially without any deformation of the longitudinally deformable elements for at least a portion of the deformation.

The longitudinal expansion of FIG. 5 and the radial contraction of FIG. 6 may be achieved in separate stages as depicted in FIGS. 5 and 6 or may be implemented at the same time or during overlapping time periods.

In an embodiment, each of one or more of the circumferentially deformable elements 6 on one of the closed rings is aligned in a direction parallel to the axis of elongation of the frame 2 with a corresponding identical one of the circumferentially deformable elements 6 on another of the closed rings when the frame 2 is in the radially expanded and longitudinally contracted state. This facilitates efficient interlocking of different closed rings in the radially expanded and longitudinally contracted state, promoting low porosity and/or high radial stiffness. In such an embodiment, the aligned circumferentially deformable elements 6 will also have the same orientation as each other. For example, in the case where each circumferentially deformable element comprises a V-shaped element, the aligned circumferentially deformable elements 6 will comprise V-shaped elements pointing in the same direction.

In an embodiment, directly adjacent closed rings will comprise circumferentially deformable elements 6 that are aligned with each other. However, the inventors have found that this configuration can lead to undesirable twisting of the frame 2 during switching from the radially expanded and longitudinally contracted state to the radially contracted and longitudinally expanded state. Twisting can be reduced by arranging for the aligned circumferentially deformable elements 6 to be separated from each other by at least one closed ring having circumferentially deformable elements 6 that are not aligned.

Figure 7:
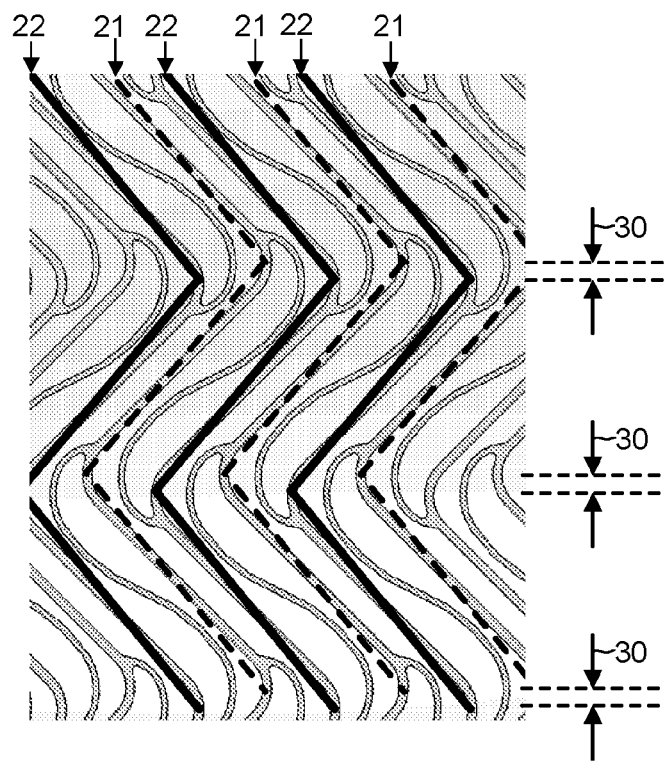
FIG. 7 depicts a portion of the frame of FIG. 3 illustrating an alternating sequence of first type and second type rings.

In an embodiment of this type, of which the embodiment of FIGS. 2-8 is an example, the closed rings form an alternating sequence of first type closed rings 21 and second type closed rings 22. The first type closed rings 21 and second type closed rings 22 are labelled in FIGS. 5-7. In FIG. 7, example circumferentially deformable elements 6 have been overlaid with thick lines to indicate the different types of closed ring. Thick broken lines indicate example circumferentially deformable elements 6 in first type closed rings 21. Thick solid lines indicate example circumferentially deformable elements 6 in second type closed rings 22.

Each of one or more of the circumferentially deformable elements 6 (e.g. V-shaped elements) on each first type closed ring 21 is aligned in a direction parallel to the axis of elongation of the frame 2 with a corresponding identical one of the circumferentially deformable elements 6 on each other first type closed ring 21 and is not aligned with a corresponding identical one of the circumferentially deformable elements on any of the second type closed rings, when the frame is in the radially expanded and longitudinally contracted state. Alternatively or additionally, each of one or more of the circumferentially deformable elements 6 (e.g. V-shaped elements) on each second type closed ring 22 is aligned in a direction parallel to the axis of elongation of the frame 2 with a corresponding identical one of the circumferentially deformable elements on each other second type closed ring 22 and is not aligned with a corresponding identical one of the circumferentially deformable elements on any of the first type closed rings 21, when the frame is in the radially expanded and longitudinally contracted state. In the particular example shown the first type closed rings 21 and the second type closed rings 22 are offset from each other circumferentially when the frame 2 is in the radially expanded and longitudinally contracted state by distance 30.

Alternatively or additionally, and also or further contributing to the reduction of twisting, the longitudinally deformable elements comprise sets of first type longitudinally deformable elements 8A and sets of identical second type longitudinally deformable elements 8B. The sets of first type longitudinally deformable elements 8A and the sets of second type longitudinally deformable elements 8B are arranged in an alternating sequence such that each first type closed ring 21 is connected to the next second type closed ring 22 in a given direction parallel to the axis of elongation exclusively by first type longitudinally deformable elements 8A and each second type closed ring 22 is connected to the next first type closed ring 21 in the same given direction parallel to the axis of elongation exclusively by second type longitudinally deformable elements 8B. An example of such an arrangement can be seen most clearly in FIG. 5. The first type longitudinally deformable elements 8A have a different shape and/or orientation from the second type longitudinally deformable elements 8B. Optionally, the first type longitudinally deformable elements 8A are mirror images of the second type longitudinally deformable elements 8B when the frame 2 is viewed in an unfolded planar state (as in FIGS. 3-8). In the example shown, the first type longitudinally deformable elements 8A curve downwards to the right and the second type longitudinally deformable elements are mirror images and curve upwards to the right.

In various embodiments, the embodiment of FIGS. 3-8 being an example, at least two of the (optionally overlapping) closed rings are identical to each other. The identical closed rings may be aligned with each other in the longitudinal direction or may be offset with respect to each other in the circumferential direction, at least in the radially expanded and longitudinally contracted state. The embodiment of FIGS. 3-8 comprises closed rings of both types: first type closed rings 21 are aligned with first type closed rings 21, second type closed rings 22 are aligned with second type closed rings 22, and first type closed rings 21 are circumferentially offset relative to second type closed rings 22.

In various embodiments, the embodiment of FIGS. 3-8 being an example, at least two of the (optionally overlapping) closed rings each consists of a plurality of identical circumferentially deformable elements connected together in the same orientation. In the particular example of FIGS. 3-8 each of the identical circumferentially deformable elements comprises a V-shaped element. More generally, the closed rings may be formed from plural straight elements, such that at least 50%, optionally at least 75%, optionally at least 85%, optionally at least 90%, optionally at least 95%, of a path along each of the at least two closed rings is formed from elements that are substantially straight. Forming the closed rings in this way helps to provide high radial stiffness.

In various embodiments, the embodiment of FIGS. 3-8 being an example, two of the closed rings 21,22 are connected to each other exclusively by a plurality of longitudinally deformable elements 8,8A,8B that can be expanded or contracted longitudinally substantially without any change in the shape of the circumferentially deformable elements forming the two closed rings 21,22. Optionally, none of the longitudinally deformable elements 8,8A,8B is connected directly to any other longitudinally deformable element. In order to spread the strain during the switching from the radially expanded and longitudinally contracted state to a radially contracted and longitudinally expanded state (or vice versa), each of one or more of the longitudinally deformable elements 8,8A,8B is curved along at least 20%, optionally along at least 50%, optionally along at least 75%, optionally along at least 90%, optionally along substantially all of, the length of the longitudinally deformable element 8,8A,8B.

In various embodiments, the embodiment of FIGS. 3-8 being an example, each of one or more of the longitudinally deformable elements 8,8A,8B is connected to one of the closed rings 21,22 at a junction 32 (depicted in FIG. 8) and configured such that an angle 34 between the longitudinally deformable element 8,8A,8B and a circumferentially deformable element 6 at the junction 32 changes by less than 30 degrees, optionally less than 20 degrees, optionally less than 10 degrees, during switching from the radially expanded and longitudinally contracted state to the radially contracted and longitudinally expanded state.

In the example of FIGS. 3-8, each circumferentially deformable element 6 is substantially V-shaped. Each closed ring thus consists of a plurality of Vs connected together at the outer ends of the arms of each V. More generally, the closed rings may be formed from plural straight elements. In such embodiments, the junctions at which the longitudinally deformable elements are connected to the closed rings of circumferentially deformable elements may be located at a point other than at the centre of a joining region where the two arms of the V join (i.e. away from all such joining regions), and at a point other than at a centre of a joining region where each straight element is joined to a neighbouring straight element (i.e. away from all such joining regions). The junction may be located away from the centre of the nearest joining region by 2% or more, optionally 5% or more, optionally 10% or more, optionally 20% or more, optionally 40% or more, of the length of at least one of the arms of the V (e.g. the length of a straight element of the V).

Figure 8:
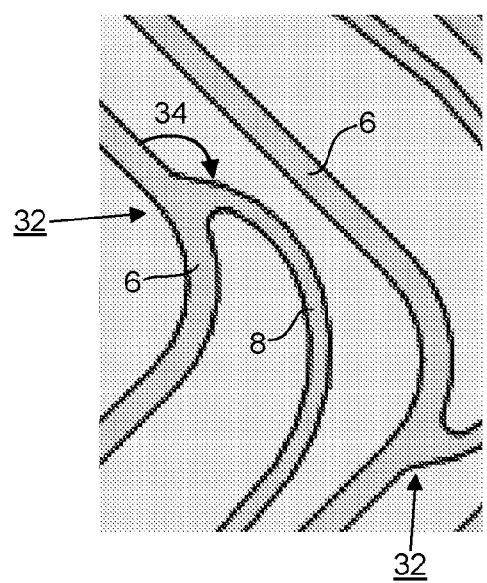
FIG. 8 depicts a portion of the frame of FIG. 7 magnified to show a junction between a circumferentially deformable element and a longitudinally deformable element.

Locating the junction away from the centre of the joining region reduces the amount of material around the junction, increasing the flexibility of the longitudinally deformable elements near the junction and allowing for greater longitudinal contraction and expansion of the tube. Locating the junction away from the centre of the joining region also makes it possible to lengthen the longitudinally deformable element, thereby spreading out (and thereby reducing) the bending stresses associated with deformation of the longitudinally deformable element more. Thus, in some embodiments, the two junctions at the respective ends of each of one or more of the longitudinal deformable elements are arranged to be on the outermost sides of the centres of the respective nearest joining regions between arms of the circumferentially deformable elements. Referring to FIG. 8 for example, a first end of a longitudinal deformable element may be connected above the centre of a joining region (as is the case for the leftmost junction 32 in FIG. 8) and a second end of the longitudinal deformable element may be connected below the centre of the joining region (as is the case for the rightmost junction 32 in FIG. 8, although the particular junction shown belongs to a different longitudinal deformable element of course).

In an embodiment, a joining point (i.e. a point at the outer ends of the arms of each V where two adjacent V-shaped elements on the same closed ring join) may be separated from an adjacent joining point on the same closed ring of circumferentially-deformable elements 6 by a separation distance. This separation distance will increase as the tube moves from the radially contracted and longitudinally expanded state to the radially expanded and longitudinally contracted state, as seen by comparing FIGS. 5 and 6. The separation distance in the radially expanded and longitudinally contracted state may be sufficiently large that one of the longitudinally deformable elements 8 and/or a V-shaped element from an adjacent closed ring of circumferentially deformable elements 6 can fit into the space between the two adjacent joining points, as seen in FIGS. 4 and 8. Thus, in an embodiment, the separation distance in the radially expanded and longitudinally contracted state is such as to allow a vertex of a V-shaped element in an adjacent closed ring located at a circumferential position lying between the circumferential positions of the two joining points (but at a different longitudinal position), and at least a portion of a longitudinally deformable element connected closest to the vertex, to move, during a transition from the frame being in the radially contracted and longitudinally expanded state to the frame being in the radially expanded and longitudinally contracted state, through a notional line joining the two joining points (i.e. so at to move from a longitudinally non-overlapping state to a longitudinally overlapping state).

To facilitate the separation distance being sufficiently large while allowing the longitudinally deformable element to be relatively long, which reduces stress concentrations, the smallest angle between the two arms of the V-shaped elements in the radially expanded and longitudinally contracted state may be larger than 60 degrees, optionally larger than 80 degrees, optionally larger than 100 degrees, optionally larger than 120 degrees.

Having a sufficiently large separation distance allows adjacent rings of circumferentially-deformable elements to move closer together in the radially expanded and longitudinally contracted state, which in turn decreases the porosity of the tube in this state and improves the performance and effectiveness of the device. Providing a relatively large separation distance makes it possible for the longitudinally deformable element to be relatively long, which advantageously spreads out stress along the longitudinally deformable element.

The tube of any of the above embodiments may be used in a method of treating an aneurysm, comprising deploying the tube over an opening to the aneurismal sac and thereby redirecting blood flow away from the aneurismal sac to promote thrombus formation in the aneurismal sac.

I claim:
1. An expandable tube for deployment within a blood vessel, comprising:
   an elongate frame that is reversibly switchable from a radially expanded and longitudinally contracted state to a radially contracted and longitudinally expanded state, wherein:
   the frame comprises a plurality of longitudinally deformable elements for providing longitudinal expansion and contraction of the frame and a plurality of circumferentially deformable elements for providing radial expansion and contraction of the frame;
   the longitudinally deformable elements can be expanded or contracted longitudinally without any change in the shape of the circumferentially deformable elements;
   the plurality of circumferentially deformable elements comprises a plurality of sets of circumferentially deformable elements, each set of circumferentially deformable elements forming a closed ring around an axis of elongation of the frame, each closed ring consisting exclusively of the circumferentially deformable elements;
   at least two of the closed rings occupy overlapping ranges of longitudinal positions when the frame is in the radially expanded and longitudinally contracted state and occupy non-overlapping ranges of longitudinal positions when the frame is in the radially contracted and longitudinally expanded state; and
   when the frame is in the radially expanded and longitudinally contracted state:
   (a) each of one or more of the circumferentially deformable elements on a first closed ring of the closed rings is aligned in a direction parallel to the axis of elongation of the elongate frame with a corresponding identical one of the circumferentially deformable elements on a second closed ring of the closed rings; and
   (b) the first closed ring and the second closed ring are separated from each other by at least one closed ring having circumferentially deformable elements that are not aligned in a direction parallel to the axis of elon- gation of the elongate frame with any of the circumferentially deformable elements of the first or second closed rings.

2. The tube of claim 1, wherein the aligned circumferentially deformable elements have the same orientation as each other.

3. The tube of claim 1, wherein the closed rings form an alternating sequence of first type closed rings and second type closed rings, wherein:
  each of one or more of the circumferentially deformable elements on each first type closed ring is aligned in a direction parallel to the axis of elongation of the elongate frame with a corresponding identical one of the circumferentially deformable elements on each other first type closed ring and is not aligned with a corresponding identical one of the circumferentially deformable elements on any of the second type closed rings, when the frame is in the radially expanded and longitudinally contracted state; and/or
  each of one or more of the circumferentially deformable elements on each second type closed ring is aligned in a direction parallel to the axis of elongation of the elongate frame with a corresponding identical one of the circumferentially deformable elements on each other second type closed ring and is not aligned with a corresponding identical one of the circumferentially deformable elements on any of the first type closed rings, when the frame is in the radially expanded and longitudinally contracted state.

4. The tube of claim 3, wherein the longitudinally deformable elements comprise sets of identical first type longitudinally deformable elements and sets of identical second type longitudinally deformable elements, wherein the sets of first type longitudinally deformable elements and the sets of second type longitudinally deformable elements are arranged in an alternating sequence such that each first type closed ring is connected to the next second type closed ring in a given direction parallel to the axis of elongation exclusively by first type longitudinally deformable elements and each second type closed ring is connected to the next first type closed ring in the same given direction parallel to the axis of elongation exclusively by second type longitudinally deformable elements, wherein the first type longitudinally deformable elements have a different shape and/or orientation from the second type longitudinally deformable elements.

5. The tube of claim 4, wherein the first type longitudinally deformable elements are mirror images of the second type longitudinally deformable elements when the frame is viewed in an unfolded planar state.

6. The tube of claim 1, wherein the at least two closed rings are identical to each other.

7. The tube of claim 6, wherein the at least two closed rings are aligned with each other in the longitudinal direction when the frame is in the radially expanded and longitudinally contracted state.

8. The tube of claim 1, wherein at least 50% of a path along each of the at least two closed rings is formed from elements that are straight.

9. The tube of claim 1, wherein two of the closed rings are connected to each other exclusively by a plurality of longitudinally deformable elements that can be expanded or contracted longitudinally without any change in the shape of the circumferentially deformable elements forming the two closed rings.

10. The tube of claim 9, wherein none of the longitudinally deformable elements is connected directly to any other longitudinally deformable element.

11. The tube of claim 1, wherein each of one or more of the longitudinally deformable elements is curved along at least 20% of the length of the longitudinally deformable element.

12. The tube of claim 1, wherein each of one or more of the longitudinally deformable elements is connected to one of the closed rings at a junction and configured such that an angle between the longitudinally deformable element and a circumferentially deformable element at the junction changes by less than 30 degrees during switching from the radially expanded and longitudinally contracted state to the radially contracted and longitudinally expanded state.

13. The tube of claim 1, wherein each of one or more of the longitudinally deformable elements is connected to one of the closed rings at a junction, the closed rings are formed from plural V-shaped elements joined together at one or more joining regions, and the junction is located away from the centre of the nearest joining region.

14. The tube of claim 13, wherein the junction is located away from the centre of the nearest joining region by more than 2% of the length of at least one of the arms of the V-shaped elements.

15. The tube of claim, wherein 1:
  the at least two closed rings each consists of a plurality of V-shaped elements, and a joining point where two adjacent V-shaped elements on one of the closed rings join to each other is separated from an adjacent joining point on the same closed ring by a separation distance; and
  the separation distance in the radially expanded and longitudinally contracted state is such as to allow a vertex of a V-shaped element in an adjacent closed ring located at a circumferential position lying between the circumferential positions of the two joining points, and at least a portion of a longitudinally deformable element connected closest to the vertex, to move, during a transition from the frame being in the radially contracted and longitudinally expanded state to the frame being in the radially expanded and longitudinally contracted state, through a notional line joining the two joining points.

16. The tube of claim 15, wherein the separation distance is such as to provide an angle between the two arms of the V-shaped element in the radially expanded and longitudinally contracted state that is larger than 60 degrees.

17. The tube of claim 1, wherein the porosity of the frame in the radially expanded and longitudinally contracted state is less than 90%.

18. A method of treating an aneurysm, comprising deploying the tube of any preceding claim in the radially expanded and longitudinally contracted state over the opening to an aneurismal sac and thereby redirecting blood flow away from the aneurismal sac to promote thrombus formation in the aneurismal sac.

* * * * *